(12) United States Patent
Sheth et al.

(10) Patent No.: US 8,537,364 B2
(45) Date of Patent: Sep. 17, 2013

(54) FIBER OPTIC MEASUREMENT OF PARAMETERS FOR DOWNHOLE PUMP DIFFUSER SECTION

(75) Inventors: Ketankumar K. Sheth, Tulsa, OK (US); Earl B. Brookbank, Claremore, OK (US); Suresha Roshani O'Bryan, Joplin, MO (US); Michael Forsberg, Claremore, OK (US)

(73) Assignee: Baker Hughes Incorporated, Houston, TX (US)

( * ) Notice: Subject to any disclaimer, the term of this patent is extended or adjusted under 35 U.S.C. 154(b) by 98 days.

(21) Appl. No.: 13/314,010

(22) Filed: Dec. 7, 2011

(65) Prior Publication Data

US 2013/0148127 A1 Jun. 13, 2013

(51) Int. Cl.
 *G01N 21/47* (2006.01)
(52) U.S. Cl.
 CPC .................................. *G01N 21/47* (2013.01)
 USPC .......................................................... 356/446
(58) Field of Classification Search
 CPC ....................................................... G01N 21/55
 USPC ................................................... 356/445–448
 See application file for complete search history.

(56) References Cited

U.S. PATENT DOCUMENTS

| | | | |
|---|---|---|---|
| 6,913,079 B2 * | 7/2005 | Tubel | 166/250.01 |
| 2003/0236626 A1 * | 12/2003 | Schroeder et al. | 702/6 |
| 2004/0141420 A1 * | 7/2004 | Hardage et al. | 367/149 |
| 2007/0041019 A1 * | 2/2007 | Schmidt | 356/480 |
| 2007/0272406 A1 * | 11/2007 | McCoy et al. | 166/250.01 |
| 2011/0002795 A1 * | 1/2011 | Brookbank | 417/63 |
| 2011/0139447 A1 * | 6/2011 | Ramos et al. | 166/254.2 |
| 2012/0026482 A1 * | 2/2012 | Dailey | 356/43 |
| 2012/0073804 A1 * | 3/2012 | Harman et al. | 166/250.01 |
| 2012/0179378 A1 * | 7/2012 | Duncan et al. | 702/8 |

* cited by examiner

*Primary Examiner* — Michael P Stafira
(74) *Attorney, Agent, or Firm* — Shawn Hunter

(57) ABSTRACT

A system for monitoring operating parameters for the pump section of an electrical submersible pump. The system includes an optic fiber associated with the pump section of an electrical submersible pump and having a sensor to detect at least one operating parameter within the pump section. The system also includes a signal analyzer operably associated with the optic fiber to receive an optical signal representative of the detected operating parameter.

7 Claims, 6 Drawing Sheets

FIBER OPTIC MEASUREMENT OF PARAMETERS FOR DOWNHOLE PUMP DIFFUSER SECTION

BACKGROUND OF THE INVENTION

1. Field of the Invention

The present invention generally relates to the measurement of operating parameters within the diffuser section of a downhole pump.

2. Description of the Related Art

Electrical submersible pumps are often used to flow hydrocarbon production fluids from subterranean locations via wellbores. A typical pump of this type includes a seal section, a motor section and a pump section. A diffuser is located within the pump section and is used to flow production fluids upwardly to the next impeller while converting velocity (kinetic energy) to the pressure (potential energy).

SUMMARY OF THE INVENTION

The present invention provides devices and methods for measuring various operating parameters associated with the pump section of an electrical submersible pump. In a described embodiment, optical fibers are incorporated into the housing of the pump section. In particular embodiments, an optical fiber is associated with one or more diffusers within the pump housing so as to measure pressure, temperature and/or vibration (strain). According to some embodiments, optical fiber Bragg gratings are used to perform the sensing function. In other embodiments, the axial end portions of optical fibers are used as discrete point sensors.

The devices and methods of the present invention permit monitoring of a number of operating parameters for the pump section of an electrical submersible pump. In one embodiment, the fluid pressure within the pump housing is measured and compared to the measured fluid pressure outside of the housing to determine the pressure differential across the pump housing. In a further described embodiment, one or more fiber optic sensors are used to detect and monitor operating parameters such as temperature and pressure within the space between the outer pump housing and one or more of the diffuser shrouds within.

In other described embodiments, optical fiber sensors are used to monitor vibration and/or stress loading associated with rotation of the impeller within the diffuser. The optic fiber sensors may be located at or near the impeller supports or a portion of the diffuser hub.

In a described embodiment, the fiber optic sensors are associated with a surface-based optic signal processor which is capable of detecting optic signals that are transmitted along the fibers and interpreting the signals. Also in a described embodiment, a display and/or a recording device are associated with the signal processor.

BRIEF DESCRIPTION OF THE DRAWINGS

The advantages and other aspects of the invention will be readily appreciated by those of skill in the art and better understood with further reference to the accompanying drawings in which like reference characters designate like or similar elements throughout the several figures of the drawings and wherein.

DETAILED DESCRIPTION OF THE PREFERRED EMBODIMENTS

Figure 1:
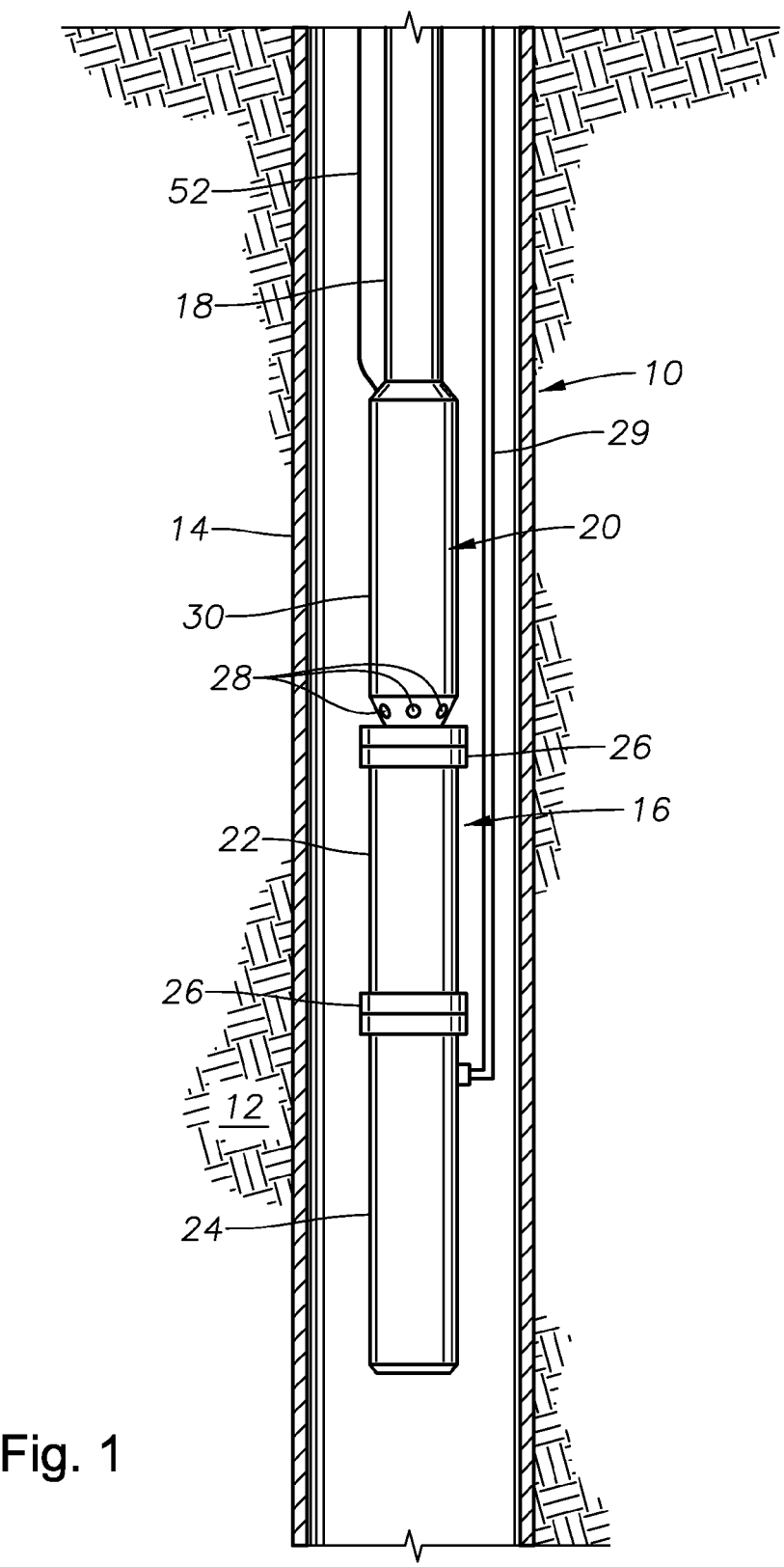
FIG. 1 is a side, partial cross-sectional view of an exemplary electrical submersible pump constructed in accordance with the present invention and within a wellbore.

FIG. 1 depicts an exemplary wellbore 10 which has been drilled within the earth 12 and which is lined with metallic casing 14, of a type known in the art. The wellbore 10 contains hydrocarbon fluid that is to be flowed toward the surface of the wellbore 10. An electrical submersible pump (ESP) 16 is shown suspended within the wellbore 10 by a running string 18 and includes a pump section 20, a seal section 22 and a motor section 24. These sections 20, 22 and 24 are preferably affixed to each other by flanged connections 26, as shown. Pump inlets 28 are formed in the pump section 20 to allow hydrocarbon fluids in the wellbore 10 to be drawn into the ESP 16.

The general construction and operation of the seal and motor sections 22, 24 are generally well known to those of skill in the art and will not be discussed in significant detail here. It is noted, however, that the seal section 22 may generally include various bladders and bellows used for equalizing the pressure of lubricant for the motor section 24. The motor section 24 typically includes an electrically-driven motor that is supplied with power from the surface via power conduit 29. A fiber optic cable 52 is illustrated extending to the pump section 20 from the surface.

Figure 2:
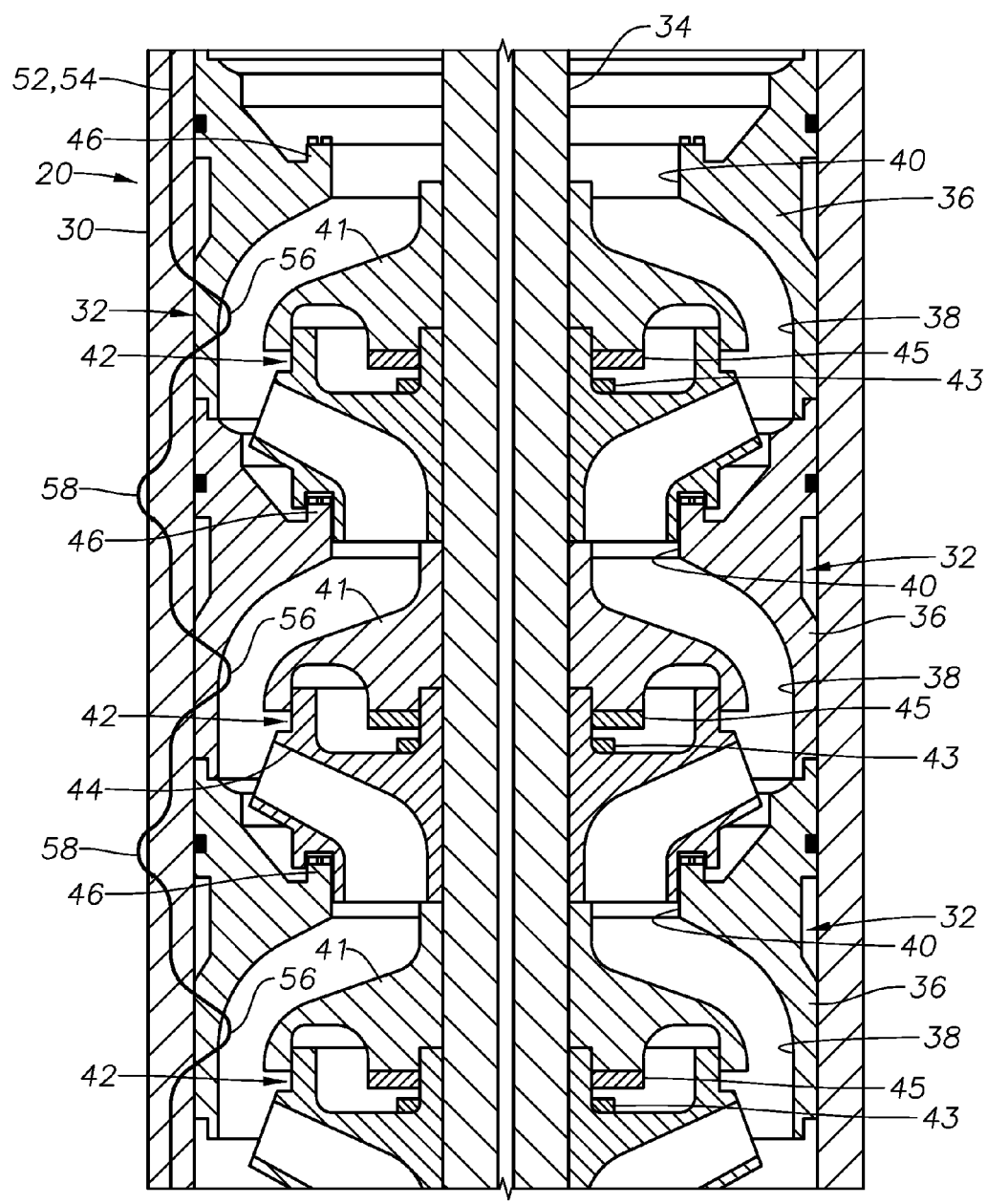
FIG. 2 is a side, cross-sectional view of the pump section of the pump shown in FIG. 1.

FIG. 2 illustrates a portion of the interior of the pump section 20 wherein the outer pump housing 30 encloses a plurality of diffusers 32 that are arranged in a stacked configuration and radially surround central shaft 34. Diffusers 32 may take several different forms depending upon the desired application, including volute, radial, mixed flow and axial designs. The general operation of diffusers is discussed in further detail in, for example, U.S. Patent Publication No. 2011/0058928 by Sheth et al. and U.S. Patent Publication No. 2011/0002795 by Brookbank. Both of these Publications are owned by the assignee of the present invention and are herein incorporated by reference in their entirety. During operation, the shaft 34 is rotated within the pump housing 30 by the motor section 24. Each diffuser 32 includes an outer radial diffuser shroud 36 that is seated within the pump housing 30 and defines a plurality of radial vanes 38. As those of skill in the art understand, the vanes 38 are radially separated from one another by partitions. The diffuser housing 36 is aligned with the shrouds 36 of adjoining diffuser shrouds 36. Fluid openings 40 are provided between neighboring vanes 38 to permit fluid to pass upwardly from one diffuser 32 to the next. Each diffuser 32 also includes a central diffuser hub 41.

Impellers 42 are mounted upon and rotate with the shaft 34. An impeller 42 is located within each diffuser 32. Upthrust washers 43 are disposed between each impeller 42 and its associated diffuser hub 41. An upthrust washer 43 will contact upthrust pad 45 as the associated impeller 42 is moved axially upwardly toward associated diffuser hub 41. Each impeller 42 includes a plurality of impeller vanes 44 which direct fluid radially outwardly and increase fluid pressure during operation. Impeller supports 46 are provided by the diffuser housing 36. As best seen in the close-up view of FIG. 4, down thrust bearings/washers 48 are disposed upon each of the impeller supports 46 and each will support an annular rotary bearing 50 on the impeller 42. As the impeller 42 is rotated within the diffuser 32, the rotary bearing 50 places some axial load upon the down thrust bearing/washer 48. In particular embodiments, a reflective surface 51 (see FIG. 4) is presented by the rotary bearing 50 so that vibration or loading of the rotary bearing 50 upon the down thrust bearing 48 can be more readily detected.

Figure 3:
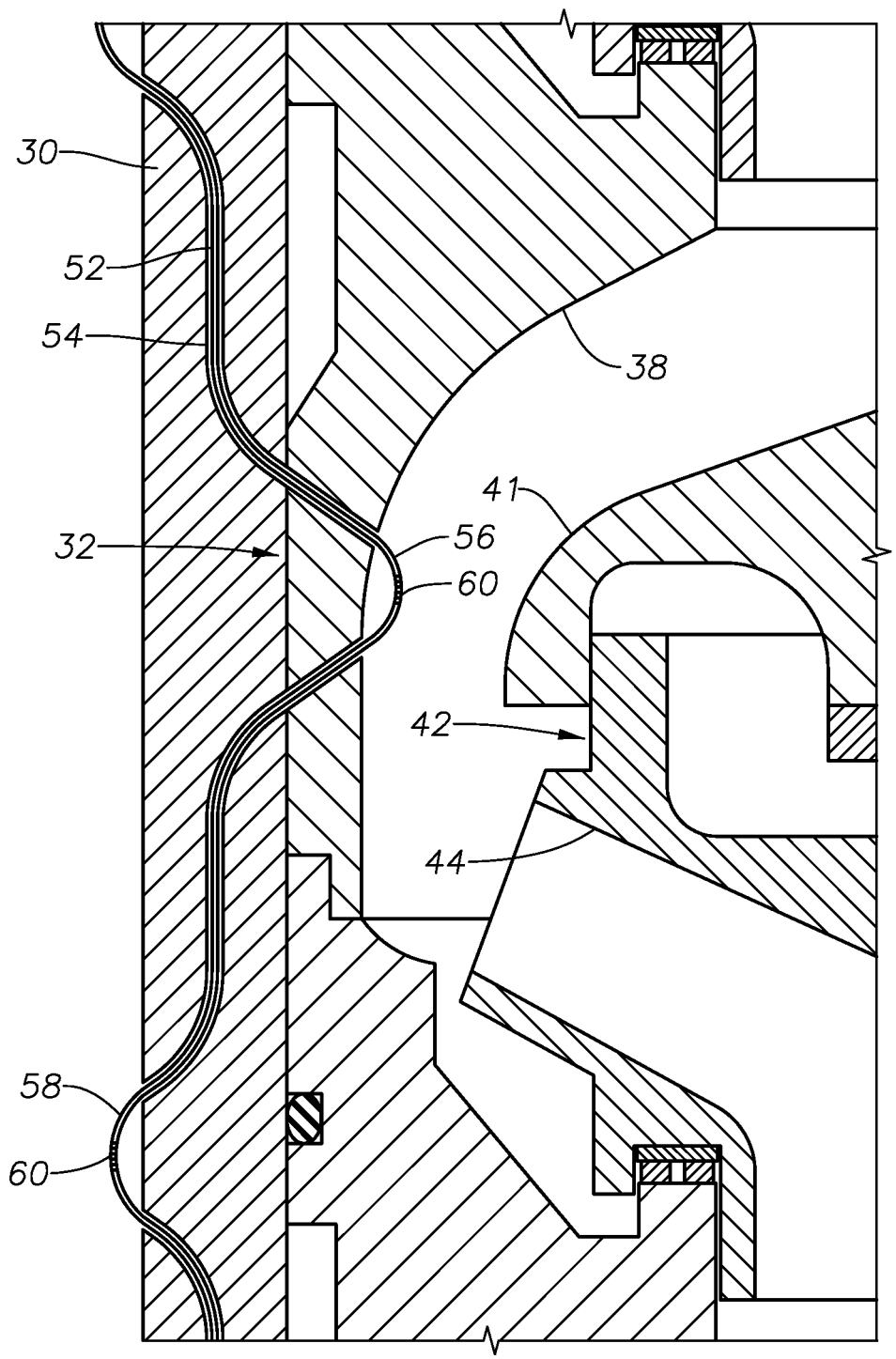
FIG. 3 is an enlarged side, cross-sectional view of portions of the diffuser section of the pump section shown in FIG. 2 and incorporating fiber optic sensors in accordance with the present invention.

FIG. 2 illustrates an exemplary optic fiber 52 which extends through bonding 54 in the outer pump housing 30 and diffuser shrouds 36. FIG. 3 is an enlarged view of portions of the pump section 20 which shows features of the fiber 52 and bonding 54 in greater detail. In the depicted embodiment, a portion of the optic fiber 52 is exposed within each diffuser 32 at locations 56. In addition, a portion of the optic fiber 52 is exposed outside of the outer pump housing 30 at locations 58. As illustrated in FIG. 3, the optic fiber 52 includes one or more suitable Bragg gratings 60 at each of the locations 56, 58. With the use of selected multiplexed Bragg gratings, the fiber 52 can detect operational parameters including temperature and pressure. Pressure is detected by the deflection and/or distortion of a pressure sensor device at a location within the fiber 52 or proximate the end of the fiber and/or proper deflector. A suitable pressure sensor arrangement for use with the fiber 52 can be constructed using a pressure responsive diaphragm (not shown) that is affixed to portions of the fiber 52 to induce strain in those portions of the fiber 52 which can be detected by changes to the Bragg gratings. The construction of such pressure sensor arrangements is well understood in the art and described in greater detail in, for example, U.S. Pat. Publication no. 2011/0002795 by Brookbank and EP 0954743 by Maron et al. In one embodiment, the pressure at locations 56 is sensed and compared to the pressure sensed at locations 58 to measure the differential pressure across the pump housing 30.

Figure 4:
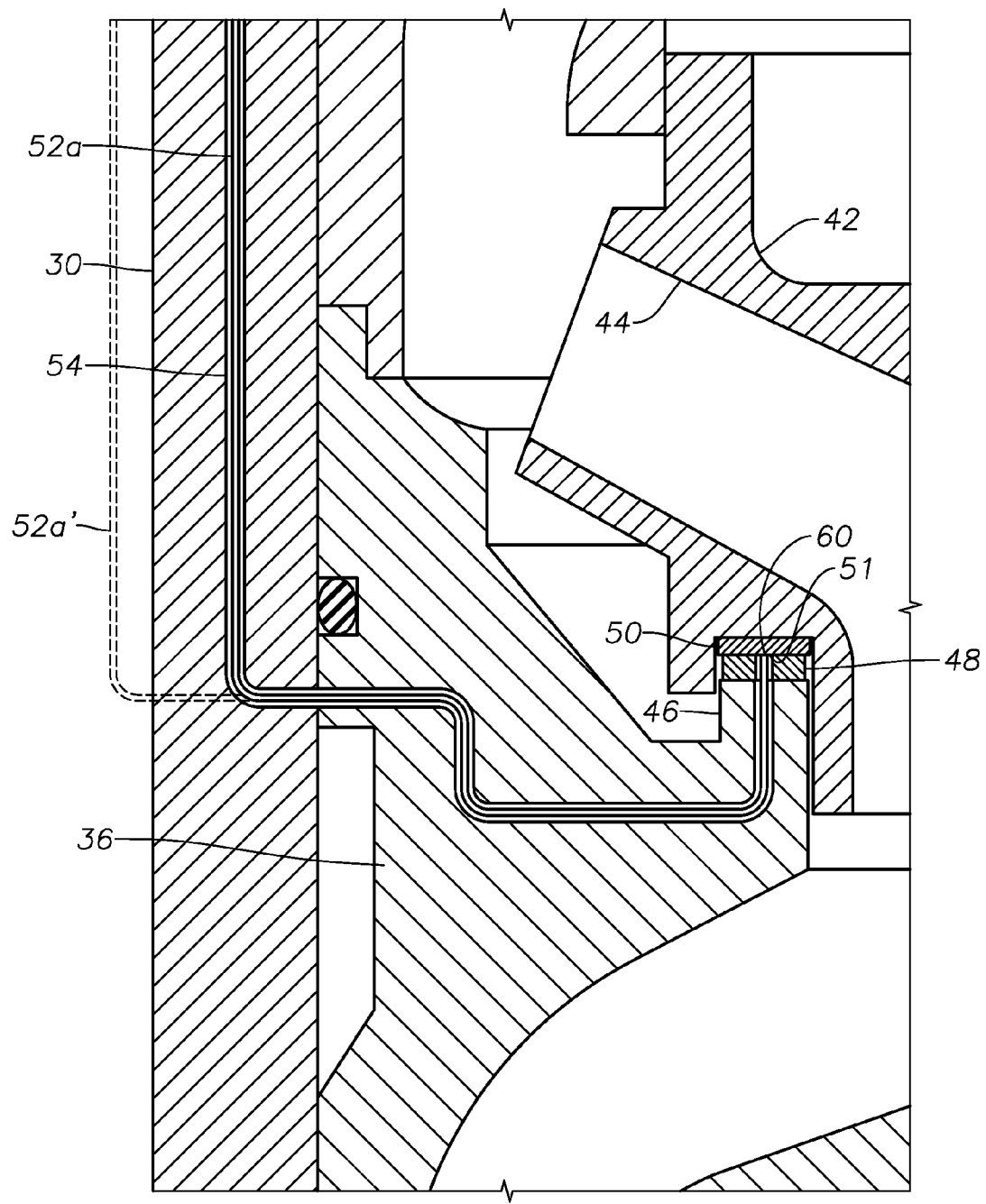
FIG. 4 is an enlarged side, cross-sectional view of a portion of a single impeller of the pump section shown in FIGS. 2-3.

In an embodiment shown in FIG. 4, an optic fiber 52a is shown extending through pump housing 30 and diffuser shroud 36 to the impeller support 46. 52A' shows an alternative pathway for the fiber that runs outside of the pump housing 30. The fiber 52a passes through the down thrust bearing/washer 48, and the end 60 of the fiber 52a contains or is associated with a sensor that will detect pressure changes resulting from loading of the thrust pad 48 by the rotary bearing 50 of the impeller 42. In operation, axial movement of the rotary bearing 50 either toward or away from the down thrust pad 48 is detected by changes in the reflection of light from the fiber 52a upon the reflective surface 51. Upthrust and downthrust of the impeller 42 of each diffuser 32 can be monitored as detected stress and, as a result, problems or potential problems can be identified.

Figure 5:
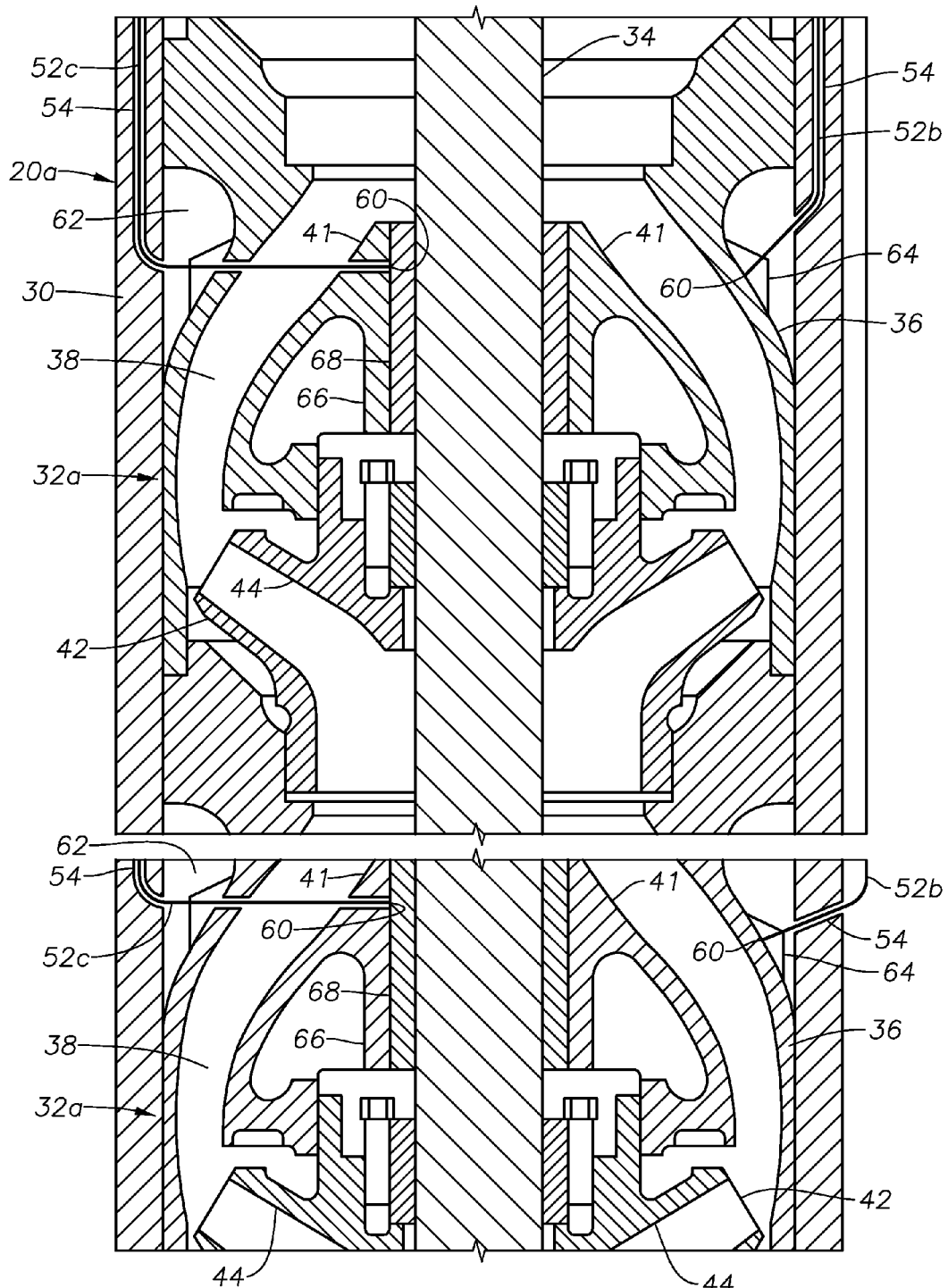
FIG. 5 is an enlarged side, cross-sectional view of portions of the diffuser section of a pump section illustrating an alternative embodiment for incorporating fiber optic sensors.

FIG. 5 illustrates an exemplary pump section 20a having a plurality of diffusers 32a contained therein. Two diffusers 32a are shown, but there may be and typically are more than two. An annular space 62 is formed between the diffuser shroud 36 and the outer pump housing 30. Optic fibers 52b extend downwardly either within or outside of the pump housing 30 and are disposed within the annular space 62 for each diffuser 32a. In the depicted embodiment, the fibers 52b are secured to the diffuser shroud 36 by retainer 64. The ends 60 of optic fibers 52b are used to detect temperature and/or pressure within the spaces 62 outside of the shrouds 36.

FIG. 5 also depicts an embodiment wherein optic fibers 52c extend down through the outer pump housing 30 and are used to detect impeller vibration for the diffusers 32a. The optic fibers 52c pass through diffuser shrouds 36, diffuser vanes 38, is diffuser hubs 41 and cylindrical bushing portion 66 of the diffuser hub 41. Sleeve 68 lies radially inside of the bushing 66 and, as the impeller 42 is rotated with respect to the diffuser shroud 36, the optic fiber ends 60 of the fibers 52c detect vibration of the impeller 42 with respect to the diffuser shroud 36 and thereby permits excessive vibration to be monitored.

Figure 6:
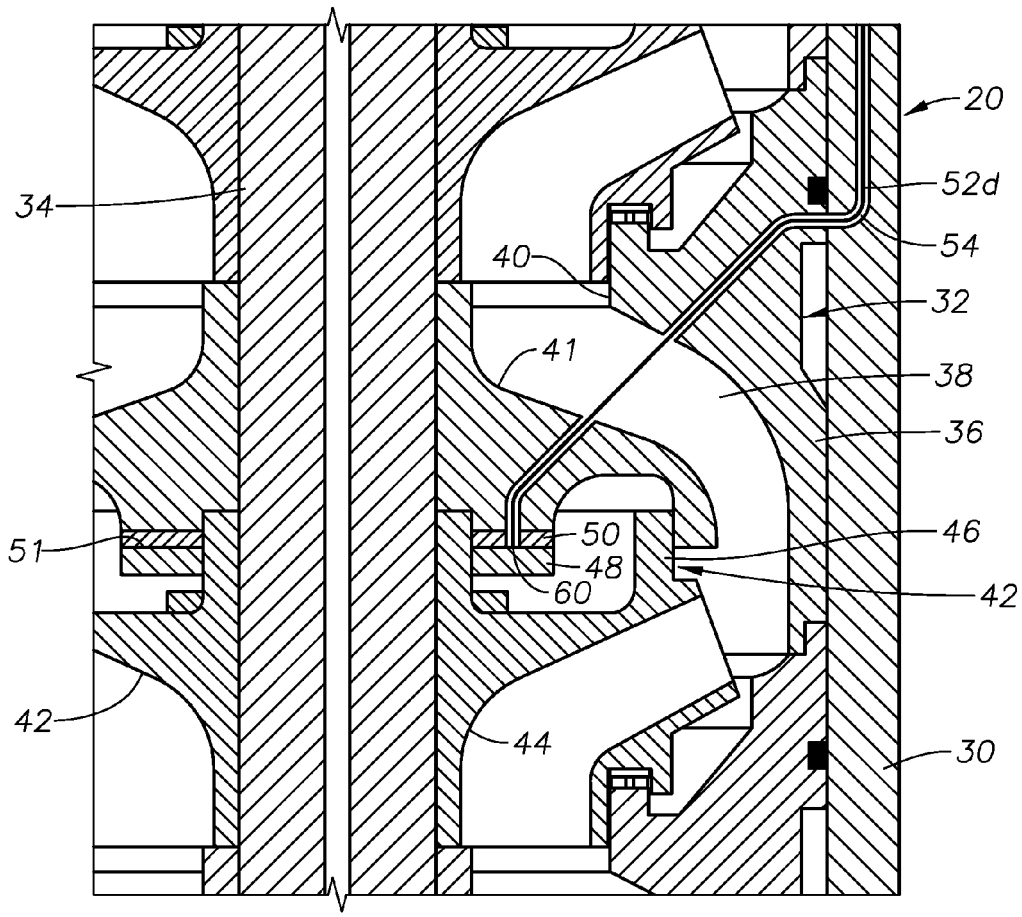
FIG. 6 is a side, cross-sectional view of the diffuser section of a pump section illustrating a further alternative embodiment for incorporating fiber optic sensors.

FIG. 6 depicts a further exemplary embodiment wherein optic fiber 52d extends through diffuser vanes 38 and into diffuser hub 41 and rotary bearing 50. The fiber end 60, having proper deflector or device, will detect pressure changes through deflection and/or distortion of a device, resulting from loading of the down thrust bearing/washer 48 by the rotary bearing 50 of the impeller 42. In particular embodiments, a reflective surface 51 is presented by the down thrust bearing/washer 48 so that stress or loading of the down thrust bearing/washer 48 upon the rotary bearing 50 can be more readily detected. Those of skill in the art will understand that the reflective surface 51 may be provided with stripes and/or color bars, which would permit light reflection into the optic fiber 52d to provide information allowing the measurement of rotational speed of the impeller 42.

Figure 7:
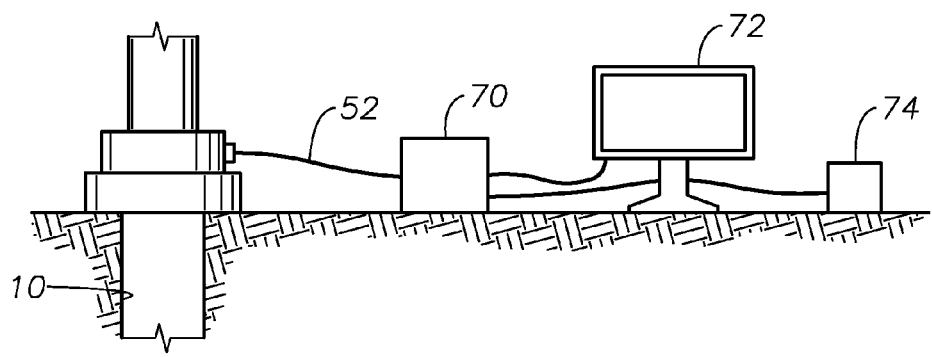
FIG. 7 is a side view of exemplary surface-based components and devices which might be used with the fiber optic sensors shown in FIGS. 1-6.

FIG. 7 is a schematic illustration of further features of an exemplary fiber optic monitoring system in accordance with the present invention and which may be associated with any of the previously described embodiments. FIG. 7 illustrates optic fiber 52, which can be representative of any of the optic fibers 52, 52a, 52b or 52c described previously. The optic fiber 52 extends from the wellbore 10 and is operably interconnected with a fiber optic signal processor 70. In some embodiments, a suitable display 72 and recording device 74 are also associated with the signal processor 70. Generally, the fiber optic signal processor is a computer or microprocessor chip that is programmed to analyze an optical signal and send information relating to the optical signal to recordable storage in the recording device 74.

Those of skill in the art will recognize that numerous modifications and changes may be made to the exemplary designs and embodiments described herein and that the invention is limited only by the claims that follow and any equivalents thereof.

What is claimed is:

1. A system for monitoring operating parameters for the pump section of an electrical submersible pump, the system comprising:
   an optic fiber associated with the pump section of an electrical submersible pump and having a sensor comprises an axial end of the optic fiber located to detect at least one operating parameter within the pump section;
   the sensor being disposed within a diffuser within the pump section to monitor axial loading between an impeller and a diffuser shroud;
   the sensor further being disposed within an impeller support within the diffuse to monitor loading by the impeller; and
   the optic fiber adapted to transmit an optical signal representative of said a eas one operating parameter to a signal analyzer.

2. The system of claim 1 further comprising a signal analyzer associated with the optic fiber to measure the at least one operating parameter.

3. The system of claim 1 further comprising a second sensor disposed outside of the diffuser shroud.

4. A system for monitoring operating parameters for the pump section of an electrical submersible pump, the system comprising:
- an optic fiber associated with the pump section of an electrical submersible pump and having a sensor located to detect at least one operating parameter within the pump section;
- the optic fiber adapted to transmit an optical signal representative of said at least one operating parameter to a signal analyzer;
- wherein the sensor is disposed within a diffuser within the pump section to monitor axial loading between an impeller and a diffuser shroud; and
- wherein the sensor is further disposed within one of a rotary bearing or a thrust bearing associated within rotation of the impeller within the diffuser shroud.

5. The system of claim 4 further comprising a signal analyzer associated with the optic fiber to measure the at least one operating parameter.

6. A system for monitoring operating parameters for the pump section of an electrical submersible pump, the system comprising:
- an optic fiber associated with the pump section of an electrical submersible pump and having a sensor located to detect at least one operating parameter within the pump section;
- the optic fiber adapted to transmit an optical signal representative of said at east one operating parameter to a signal analyzer;
- wherein the sensor comprises an axial end of the optic fiber and the sensor is disposed upon a diffuser shroud of a diffuser to detect the operating parameter to monitor vibration between an impeller and the diffuser shroud; and
- wherein the sensor is disposed within a bushing portion of a diffuser hub.

7. The system of claim 6 further comprising a signal analyzer associated with the optic fiber to measure the at least one operating parameter.

* * * * *

UNITED STATES PATENT AND TRADEMARK OFFICE
CERTIFICATE OF CORRECTION

PATENT NO.       : 8,537,364 B2  
APPLICATION NO.  : 13/314010  
DATED            : September 17, 2013  
INVENTOR(S)      : Sheth et al.

Page 1 of 1

It is certified that error appears in the above-identified patent and that said Letters Patent is hereby corrected as shown below:

In the Claims

Claim 1, column 4, line 66, the words "a eas one" should read -- at least one --.

Signed and Sealed this
Twenty-second Day of October, 2013

Teresa Stanek Rea
*Deputy Director of the United States Patent and Trademark Office*